United States Patent

Guillaumet et al.

[11] Patent Number: 5,919,814
[45] Date of Patent: Jul. 6, 1999

[54] HETEROCYCLIC COMPOUNDS

[75] Inventors: Gérald Guillaumet, Saint Jean le Blanc; Isabelle Charton, Yerres; Ahmed Mamai, Orleans; Pierre Renard, Versailles; Bruno Pfeiffer, Saint leu la Foret; Philippe Delagrange, Issy les Moulineaux; Béatrice Guardiola, Saint Cloud, all of France

[73] Assignee: Adir et Compagnie, Courbevoie, France

[21] Appl. No.: 09/066,235

[22] Filed: Apr. 24, 1998

[30] Foreign Application Priority Data

Apr. 25, 1997 [FR] France ................... 97 05110

[51] Int. Cl.⁶ ................ C07D 327/06; C07D 355/04
[52] U.S. Cl. ............. 514/432; 514/434; 514/452; 514/456; 549/15; 549/23; 549/366; 549/399; 549/407
[58] Field of Search ................. 514/434, 432, 514/452, 456; 549/15, 23, 366, 399, 407

[56] References Cited

U.S. PATENT DOCUMENTS 5,371,103  12/1994  Guillaumet .............. 514/430

Primary Examiner—D. Margaret M. Mach

Attorney, Agent, or Firm—The Firm of Gordon W. Hueschen

[57] ABSTRACT

The invention relates to compound of general formula (I):

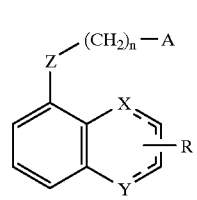

wherein:
Z represents O or CH$_2$
n is from 0 to 4
R, X and Y are as defined in the description, and
A represents

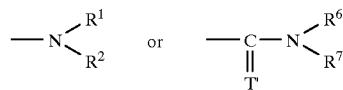

wherein R$^1$, R$^2$, R$^6$, R$^7$ and T' are as defined in the description,
and medicinal products containing the same are useful in treating or in preventing melatoninergic disorders.

15 Claims, No Drawings

HETEROCYCLIC COMPOUNDS

DESCRIPTION OF THE PRIOR ART 2,3-dihydrobenzodioxin carboxamides having a branched chain are known from the prior art (WO 9 603 378) as acyl CoA transferase inhibitors for use in the treatment of arteriosclerosis.

Also known are a large number of 2,3-dihydrobenzodioxin carbamates (EP 38 945, FR 1 494 650) and benzodithline carbamates (U.S. Pat. No. 3,636,047) for use as herbicides, insecticides or acaricides.

2,3-dihydrobenzodioxin amides (EP 669 331) are furthermore described in the literature for the treatment of schizophrenia.

Benzodioxin, chroman and thiochroman compounds directly benzo-substituted by amides or carboxamides are described as synthesis intermediates (Journal of Heterocyclic Chemistry, 1973, 10(4), pp. 623–9; EP 79 683) or for use as anxiolytic agents or antidepressants (FR 2 360 305), as neuroleptic agents (DE 3 702 005) or as dopaminergic antagonists (WO 8 403 281).

BACKGROUND OF THE INVENTION

The new compounds have proved to be powerful ligands for melatoninergic receptors.

In the last ten years, numerous studies have demonstrated the major role played by melatonin (5-methoxy-N-acetyltryptamine) in the control of the circadian rhythm and of endocrinal functions. In addition, melatonin receptors have been characterised and located.

In addition to their beneficial action on circadian rhythm disorders (J. Neurosurg. 1985, 63, pp. 321–341) and sleep disorders (Psychopharmacology, 1990, 100, pp. 222–226), ligands for the melatoninergic system have valuable pharmacological properties in respect of the central nervous system, especially anxiolytic and antipsychotic properties (Neuropharmacology of Pineal Secretions, 1990, 8 (3–4), pp. 264–272) and analgesic properties (Pharmacopsychiat., 1987, 20, pp. 222–223) and also for the treatment of Parkinson's disease (J. Neurosurg. 1985, 63, pp. 321–341) and Alzheimer's disease (Brain Research, 1990, 528, pp. 170–174). Those compounds have also exhibited activity in respect of certain cancers (Melatonin—Clinical Perspectives, Oxford University Press, 1988, pp. 164–165), ovulation (Science 1987, 227, pp. 714–720) and diabetes (Clinical Endocrinology, 1986, 24, pp. 359–364), and in the treatment of obesity (International Journal of Eating Disorders, 1996, 20 (4), pp. 443–446).

Compounds providing the means of action on the melatoninergic system are accordingly excellent medicaments for the clinician for the treatment of pathologies associated with the melatoninieLgic system, especially those mentioned above.

DETAILED DESCRIPYION OF THE INVENTION

The invention relates more specifically to compounds of formula (I)

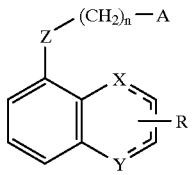

(I)

wherein:
X and Y, which may be identical or different, each represents a sulphur atom, an oxygen atom, or a $CH_q$ (where q is 0, 1 or 2), SO or $SO_2$ group, with the proviso that X and Y cannot simultaneously represent a $CH_q$ (where q is 0, 1 or 2) group,
Z represents an oxygen atom or a $CH_2$ group,
n is 0, 1, 2, 3 or 4,
A represents
a grouping

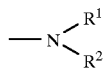

wherein
$R^1$ represents a hydrogen atom or a linear or branched $(C_1–C_6)$-alkyl group,
and $R^2$ represents a grouping

wherein T represents a sulphur atom or an oxygen atom and $R^3$ represents
an $R'^3$ group representing a hydrogen atom, an optionally substituted linear or branched $(C_1–C_6)$-alkyl group, an optionally substituted linear or branched $(C_2–C_6)$-alkenyl group, an optionally substituted linear or branched $(C_2–C_6)$-alkynyl group, a $(C_3–C_8)$-cycloalkyl group, a substituted $(C_3–C_8)$-cycloalkyl group, a cycloalkylalkyl group, a substituted cycloalkylalkyl group, an aryl group or an arylalkyl group,
or a grouping

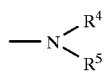

wherein $R^4$ represents a hydrogen atom or a linear or branched $(C_1–C_6)$-alkyl group and $R^5$ represents a hydrogen atom, an $R'^5$ group representing an optionally substituted linear or branched $(C_1–C_6)$-alkyl group, an optionally substituted linear or branched $(C_2–C_6)$-alkenyl group, an optionally substituted linear or branched $(C_2–C_6)$-alkynyl group, a $(C_3–C_8)$-cycloalkyl group, a substituted $(C_3–C_8)$-cycloalkyl group, a cycloalkylalkyl group, a substituted cycloalkylalkyl group, an aryl group or an arylalkyl group, or a grouping

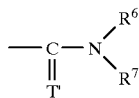

wherein T' represents a sulphur atom or an oxygen atom,
R⁶ represents a hydrogen atom or a linear or branched ($C_1$–$C_6$)-alkyl group
and R⁷ represents a hydrogen atom, an optionally substituted linear or branched ($C_1$–$C_6$)-alkyl group, an optionally substituted linear or branched ($C_2$–$C_6$)-alkenyl group, an optionally substituted linear or branched ($C_2$–$C_6$)-alkynyl group, a ($C_3$–$C_8$)-cycloalkyl group, a substituted ($C_3$–$C_8$)-cycloalkyl group, a cycloalkylalkyl group, a substituted cycloalkylalkyl group, an aryl group or an arylalkyl group,
R represents a hydrogen atom, an optionally substituted linear or branched ($C_1$–$C_6$)-alkyl group, an aryl group or an arylalkyl group,
the representation

denotes that those bonds may be single or double, it being understood that two adjacent bonds cannot simultaneously be double and that the valency of the atoms is respected,
and wherein:
the term "aryl" denotes a phenyl or naphthyl group optionally substituted by one or more halogen atoms, one or more OH, linear or branched ($C_1$–$C_6$)-alkyl, linear or branched ($C_1$–$C_6$)-alkoxy, cyano, nitro, amino and/or trihaloalkyl groups,
the term "arylalkyl" denotes a linear or branched ($C_1$–$C_6$)-alkyl group substituted by an aryl group as defined above,
the term "cycloalkylalkyl" denotes a linear or branched ($C_1$–$C_6$)-alkyl group substituted by one or more ($C_3$–$C_8$)-cycloalkyl groups,
the term "substituted" govering the terms "alkyl", "alkenyl" and "alkynyl" denotes that that group is substituted by one or more halogen atoms, one or more OH groups and/or alkoxy groups,
the term "substituted" governing the terms "cycloalkyl" and "cycloalkylalkyl" denotes that the cyclic moiety is substituted by one or more halogen atoms, one or more linear or branched ($C_1$–$C_6$)-alkyl, linear or branched ($C_1$–$C_6$)-alkoxy, phenyl, hydroxy and/or oxo groups,
with the proviso that
when X and Z simultaneously represent a $CH_2$ group, R represents a hydrogen atom and A represents a $NR^1R^2$ group, Y cannot represent an oxygen atom,
when Z represents an oxygen atom, n is other than zero,
when Z represents an oxygen atom and n is 1, A cannot represent a $CONEt_2$ grouping,
when Z represents a $CH_2$ group, n is 1 and A represents a —$NR^1CSNR^4R^5$ grouping, $R^5$ cannot represent an aryl group,
when X and Y simultaneously represent an oxygen atom and the broken-line bonds are saturated, and R represents a hydrogen atom or a $CH_2OH$ group, then A is other than an $NR^1R^{2a}$ grouping wherein $R^1$ is as defined hereinbefore and $R^{2a}$ represents an optionally substituted benzoyl group, their enantiomers and diastereolsomers, and also the addition salts thereof with a pharmaceutically acceptable acid or base.

Among the pharmaceutically acceptable acids there may be mentioned by way of non-limiting example hydrochloric, hydrobromic, sulphuric, phosphonic, acetic, trifluoroacetic, lactic, pyruvic, malonic, succiniic, glutaric, fumaric, tartaric, maleic, citric, ascorbic, methanesulphonic, camphoric acid etc.

Among the pharmaceutically acceptable bases there may be mentioned by way of non-limiting example sodium hydroxide, potassium hydroxide, triethylamine, tert-butylamine etc.

Preferred compounds of the invention are those wherein:

X and Y simultaneously represent an oxygen atom,

X represents a sulphur atom and Y represents an oxygen atom,

X represents a sulphur or oxygen atom and Y represents a $CH_q$ (where q is 0, 1 or 2) group, Z represents an oxygen atom, Z represents a $CH_2$ group, R represents a hydrogen atom.

Preferred substituents A of the invention are:

the —$NR^1COR^3$ grouping wherein $R^1$ and $R^3$ are as defined hereinbefore, and the —$CONR^6R^7$ grouping wherein $R^6$ and $R^7$ are as defined hereinbefore.

The invention relates more especially to benzodioxin, dihydrobenzodioxin, benzoxathiine, dihydrobenzoxathiine, benzopyran, dihydrobenzopyran, benzothiopyran and dihydrobenzothiopyran compounds.

More especially, the invention concerns compounds of formula (I) which are:

N-methyl-[4-(2,3-dihydro-1,4-benzoxathiin-5-yl)] butanamide,

N-ethyl-[4-(2,3-dihydro-1,4-benzoxathiin-5-yl)] butanamide,

N-[3-(1,4-benzodioxin-5-yl)propyl] butanamide,

N-methyl-[4-(2,3-dihydro-1,4-benzodioxin-5-yl)] butanamide.

Enantiomers and diastereoisomers and also the addition salts thereof with a pharmaceutically acceptable acid or base of preferred compounds of the invention are integral part of the invention.

The invention relates also to a process for the preparation of a compound of formula (I) which is characterised in that there is used as starting material a compound of formula (II):

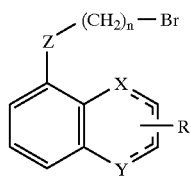

(II)

wherein X, Y, Z, R and n are as defined hereinbefore, which is subjected in succession to the action of a phthalimide and to hydrazinylosis to yield a compound of formula (III):

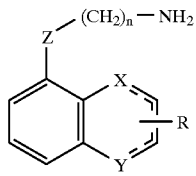

(III)

wherein X, Y, Z, n and R are as defined hereinbefore, it being possible for compound (III) furthermore to be obtained starting from compound (II) by the action of a cyanide salt or an azide followed by reduction, which compound (III) is condensed with:

an acyl chloride of formula (IV)

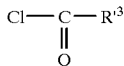

(IV)

wherein $R'^3$ is as defined hereinbefore, or with a corresponding acid anhydride (mixed or symmetrical), to obtain a compound of formula (I/a):

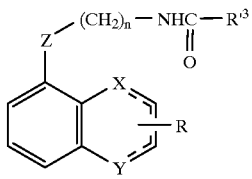

(I/a)

wherein X, Y, Z, n, R and $R'^3$ are as defined hereinbefore, a particular case of compounds of fonnula (I), which may be subjected to the action of a thionisation agent, such as Lawesson's reagent, to obtain a compound of fomnula (I/b):

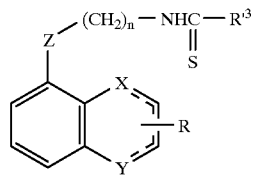

(I/b)

wherein X, Y, Z, n, R and $R'^3$ are as defined hereinbefore, a particular case of compounds of formula (I), or with a compound of formula (V)

$$T=C=N-R^5 \qquad (V)$$

wherein T and $R^5$ are as defined hereinbefore, in order to obtain a compound of formula (I/c):

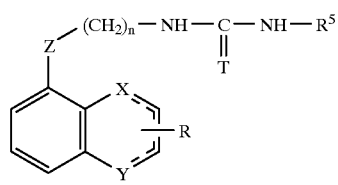

(I/c)

wherein X, Y, Z, n, R, T et $R^5$ are as defined hereinbefore, a particular case of compounds of formula (I).

the totality of the compounds (I/a), (I/b) and (I/c) constituting the compound of formula (I/d):

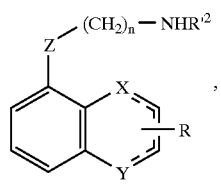

(I/d)

a particular case of compounds of formula I, wherein X, Y, Z, n and R are as defined hereinbefore and $R'^2$ represents a grouping

wherein T and $R'^3$ are as defined hereinbefore or a grouping

wherein T and $R^5$ are as defined hereinbefore, which compound (I/d) may be alkylated according to a conventional alkylation technique with a compound of formula (VI):

Alk—W  (VI)

wherein Alk represents a linear or branched ($C_1$–$C_6$)-alkyl group and W represents a leaving group, such as a halogen atom or a tosyl group, or with a dialkyl sulphate, to yield a compound of foimula (I/e.):

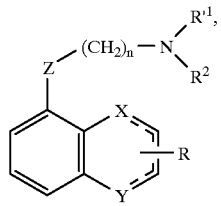

(I/e)

a particular case of compounds of formula (I), wherein X, Y, Z, n, R and $R^2$ are as defined hereinibefore and $R'^1$ represents a linear or branched ($C_1$–$C_6$)-alkyl group, or which is subjected in succession to the action of a carboxylic acid salt then to hydrolysis to yield a compound of formula (VII):

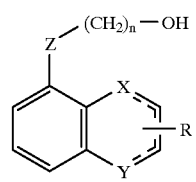

(VII)

wherein X, Y, Z, n and R are as defined hereinbefore, which is:

either oxidised to the corresponding aldehyde to obtain a compound of formula (VIII):

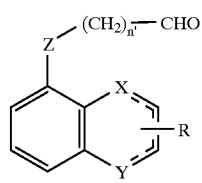

(VIII)

wherein X, Y, Z and R are as defined hereinbefore, and n' is 0, 1, 2 or 3, which is oxidised to the corresponding acid and then subjected to the action of an amine $H_2NR^7$ wherein $R^7$ is as defined hereinbefore, to yield a compound of formula (I/f):

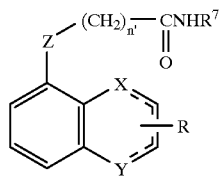

(I/f)

wherein X, Y, Z, n', R and $R^7$ are as defined hereinbefore, a particular case of compounds of formula (I), which may be subjected to the action of a thionisation agent, such as Lawesson's reagent, to obtain a compound (I/g)

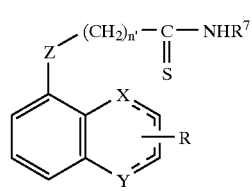

(I/g)

wherein X, Y, Z, n', R and $R^7$ are as defined hereinbefore, a particular case of compounds of formula (I), the totality of the compounds (I/f) and (I/g) constituting the compound of formula (I/h)

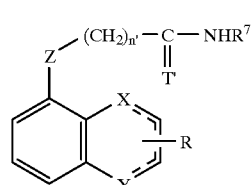

(I/h)

wherein X, Y, Z, T', n', R and $R^7$ are as defined hereinbefore, which compound (I/h) may be alkylated accordina to a conventional alkylation technique to yield a compnoud of formula (I/i):

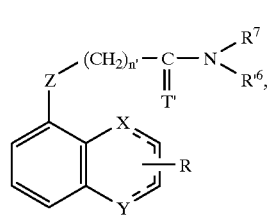

(I/i)

particular case of compounds of formula (I), wherein X, Y, Z, T', n', R and $R^7$ are as defined hereinbefore and $R'^6$ represents a liniear or branched ($C_1$–$C_6$)-alkyl group, or converted into a leaving group, such as a tosylate, then substituted with a cyanide to yield a compound of formula (IX):

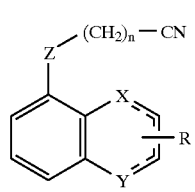

(IX)

wherein X, Y, Z, R and n are as defined hereinbefore, which is subjected in succession to hydrolysis and to condensation with an amine $H_2NR^7$ to yield a compound of formula (I/j):

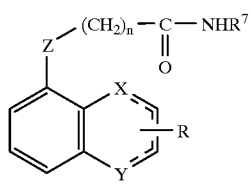
(I/j)

wherein X, Y, Z, n, R and R⁷ are as defined hereinbefore, a particular case of compounds of formula (I).
which may be subjected to a thionisation agent, such as Lawesson's reagent, to obtain a coimpound (I/k):

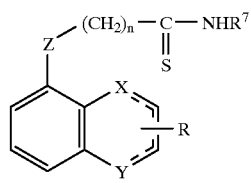
(I/k)

wherein X, Y, Z, n, R and R⁷ are as defined hereinbefore, a particular case of compounds of formula (I),
the totality of the compounds (I/j) and (I/k) constituting the compound of formula (I/l):

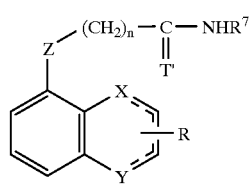
(I/l)

wherein X, Y, Z, n, T', R and R⁷ are as defined hereinbefore, a paiticular case of compounds of formula (I)
which may be alkylated according to a conventional alkylation technique to yield a compound of formula (I/m):

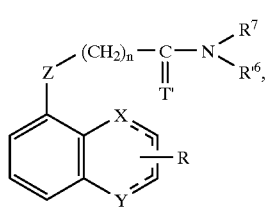
(I/m)

a paiticular case of compounds of formula (I), wherein X, Y, Z, n, T', R and R⁷ are as defined hereinbefore and R'⁶ represents a linear or branched ($C_1$–$C_6$)-alkyl group,
or with an azide followed by reduction, to yield a compound of formula (III),
the totality of the compounds (I/a) to (I/m) constituting the compounds of the general formula (I), which may be putfted accordinlt to a conventional purification technique, are separated, where appropriate, into their isomers according to a conventional separation technique, or are converted, if desired, into the addition salts thereof with a pharmaceutically acceptable acid or base.

The compounds of formula (II) are obtained starting from compounds of formula (X):

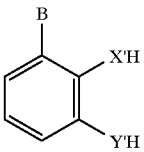
(X)

wherein B represents a methyl, CHO, COOH or methoxy group, and X' and Y', which may be identical or different, each represents an oxygen or sulphur atom, which is condensed with dibromoethane to yield a compound of formula (XI):

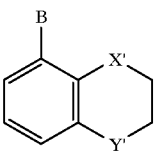
(XI)

wherein B, X' and Y' are as defined hereinbefore, which compound (XI):
  a) when B represents a methyl group, is subjected to the action of a bromination agent, such as N-bromosuccinimide, to yield a compound of formula (XII):

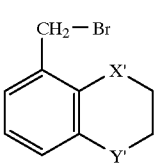
(XII)

wherein X' and Y' are as defined hereinbefore,
  b) when B represents a CHO group, is subjected to the action of a phosphorus ylide of formula (XIII):

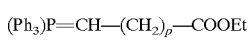
(XIII)

wherein p is 0, 1 or 2,
then to reduction, to yield a compound of formula (XIV):

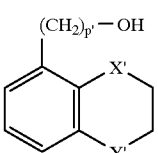
(XIV)

wherein p' is 3, 4 or 5 and X' and Y' are as defined hereinbefebore, which is substituted by a bromine atom to yield a compound of formula (XV):

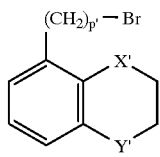

(XV)

wherein p', X' and Y' are as defined hereinbefore, a particular case of compounds of formula (II),
c) when B represents a COOH group, is subjected in succession to esterification, oxidation of the heterocycle nucleus, and reduction of the ester function to yield a compound of formula (XVI):

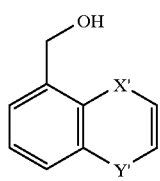

(XVI)

where X' and Y' are as defined hereinbefore,
which is either substituted by a bromine atom, or oxidised to the corresponding aldehyde, to obtain homologues having a longer chain,
d) when B represents a methoxy group, is subjected to demethylation followed by condesation with a dihalogenated compound of formula (XVII):

Hal—(CH$_2$)$_n$—Hal'  (XVII)

where n is as defined hereinbefore, and Hal and Hal' represent a halogen atom,
to yield a i ncompound of for mula (XVIII):

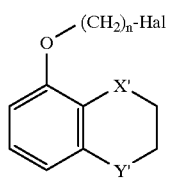

(XVIII)

wherein n, X', Y' and Hal are as defined hereinbefore, a particular case of compounds of folmula (II).
The compounds of formula (II) are furthermore obtained starting from a compound of formula (XIX):

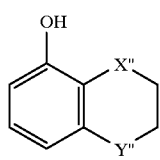

(XIX)

wherein X" represents a sulphur atom or an oxygen atom and Y" represents a CH$_2$ group,
or X" represents a CH$_2$ group and Y" represents a sulphur or oxygen atom, which is condensed with a dihalogenated compound of formula (XVII) to yield a compound of formula (XX):

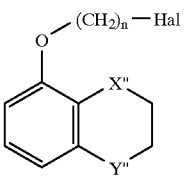

(XX)

wherein n, X", Y" and Hal are as defined hereinbefore, a particular case of compounds of formula (II),
or starting from a compound of formula (XXI)

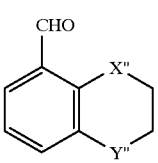

(XXI)

wherein X" and Y" are as defined hereinbefore,
which is subjected in succession to a Wittig reaction, reduction and then substitution by a bromine atom to yield a compound of formula (XXII):

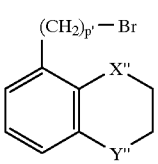

(XXII)

wherein p', X" and Y" are as defined hereinbefore, a particular case of compounds of folmula (II),
the substitution on the heterocycle being achieved by conventional methods applied to the starting compound of formula (II) or to the compound of formula (I).

The compounds of formula (I) have very valuable pharmacological properties for the clinician.

The compounds of the invention and pharmaceutical compositions containing them have proved beneficial in the treatment of disorders of the melatoninergic system.

A pharmacological study of the compounds of the invention has in fact shown them to be nontoxic, to have a very high selective affinity for melatonin receptors and to possess important activities in respect of the central nervous system and, in particular, therapeutic properties in relation to sleep disorders, anxiolytic, antipsychotic and analgesic properties and activity on the microcirculation, enabling it to be established that the products of the invention are useful in the treatment of stress, sleep disorders, anxiety, seasonal affective disorder, cardiovascular pathologies, insomnia and fatigue resulting from jet lag, schizophrenia, panic attacks, melancholia, disorders of the appetite, obesity, insomnia, psychotic disorders, epilepsy, diabetes, Parkinson's disease, senile dementia, various disorders associated with normal or pathological ageing, migraine, memory loss, Alzheimer's disease, and also cerebral circulation disorders.

In another field of activity, in the treatment the products of the invention appear to have ovulation inhibiting, properties and immunomodulating properties and it appears possible for them to be used in the treatment of cancers.

The compounds will preferably be used in the treatment of seasonal affective disorder, sleep disorders, cardiovascular pathologies, insomnia and fatigue resulting from jet lag, appetite disorders and obesity.

For example, the compounds of the invention will be used in the treatment of seasonal affective disorder and sleep disorders.

The present invention relates also to pharmaceutical compositions containing a compound of formula (I) in combination with one or more pharmaceutically acceptable excipients.

Among the pharmaceutical compositions according to the invention there may be mentioned more especially those which are suitable for oral, parenteral, nasal, percutaneous, transcutaneous, rectal, perlingual, ocular or respiratory administration and especially tablets, dragées, sublingual tablets, sachets, paquets, gelatin capsules, glossettes, lozenges, suppositories, creams, ointments, dermal gels and drinkable or injectable ampoules etc.

The dosage varies accordin, to the sex, age and weight of the patient, the administration route, the nature of the therapeutic indication, or possible associated treatments, and ranges from 0.01 mg to 1 g per 24 hours in 1 or more administrations.

The Examples which follow illustrate the invention but do not limit it in any way.

Preparation 1: 5-Bromomethyl-2,3-dihydro-1,4-benzodioxin

Step A: 5-Methyl-2,3-dihydro-1,4-benzodioxin

Dry potassium carbonate (0.93 eq.) is added to a solution of ortho-methylcatechol (10 g) dissolved in 150 ml of acetone under an argon atmosphere; the reaction mixture is heated to a gentle reflux and dibromoethane (0.4 eq.) is then added. Those operations are repeated twice at 15 minute intervals and in identical proportions (that is to say, in total 2.8 eq. of $K_2CO_3$ and 1.2 eq. of dibromoethane are added). After 12 hours' reflux, the latter is again introduced into the reaction mixture in an altogether identical amount (that is, 1.2 eq.). Heating is continued for 72 hours. The solution obtained is cooled, the salts are then filtered off over Celite and the filtrate is concentrated, hydrolysed with 60 ml of water and then extracted with dichloromethane. The recovered organic phase is washed with a 5% sodium hydroxide solution, dried over magnesium sulphate and evaporated. The cyclised product is purified over a flash silica column eluted with a 2:8 AcOEt/PE mixture (PE=petroleum ether). Yellow oil.

Step B: 5-Bromomethyl-2,3-dihydo-1,4-benzodioxin

Bromination of the 5-methyl-2,3-dihydro-1,4-benzodioxin (4 g; 27 mmol) is carried out in anhydrous carbon tetrachloride (100 ml) under an argon atmosphere, N-bromosuccinimide (4.98 g; 28 mmol; 1.05 eq.) and also a spatula tip of 2,2'-azabisisobutyronitrile being introduced in succession into the reaction mixture. The latter is heated at reflux for 6 hours by means of a lamp (60 watts). At roon temperature, the succinimide formed is filtered off, and the concentrated filtrate is purified over a flash silica column eluted with petroleum ether and then with a 1:9 AcOEt/PE mixture.

Melting point=69° C.

Preparation 2: Ethyl 3-(2,3-dihydro-1,4-benzodioxin-5-yl)propionate

Step A: 5-Formyl-2,3-dihydro-1,4-benizodioxin

The procedure is as for Step A of Preparation 1. The cyclised product is purified over a silica column eluted with a 3:7 AcOEt/PE mixture.

Melting point: 61° C.

Step B: 5-(2-Ethoxycarbonylethylene)-2,3-dihydro-1,4-benzodioxin

The 5-formyl-2,3-dihydro-1,4-benzodioxin is dissolved in toluene, and ethoxycarbonylmethylenetriphenylphosphorane (2.2 eq.) is introduced. The reaction mixture is heated at reflux for 4 hours. The triphenylphosphine oxide formed is then precipitated in the cold in the presence of hexane. The concentrated filtrate is purified directly over a silica column, AcOEt/PE (1:9).

Step C: Ethyl 3-(2,3-dihydro-1,4-benzodioxin-5-yl)propionate

The 5-(2-ethoxycarbonylethylene)-2,3-dihydro-1,4-benzodioxin is dissolved in ethanol (20 ml) then introduced into the reactor of a Paar apparatus. 10% (by weight) palladium-on-carbon is then added. The double bond is hydrogenated under a pressure of 45 psi for 12 hours. The catalyst is removed by filtration and then the solvent is evaporated off. The residual oil is purified over a silica column eluted with a 3:7 AcOEt/PE mixture. Colourless oil.

Preparation 3: 3-[(2,3Dihydro-1,4-benzodioxin-5-yl)propyl] 4-methyl-1-benzenesulphonate Step A: 3-(2,3-Dihydro-1,4-benizodioxin-5-yl)propanol A solution of the compound obtained in Preparation 2 (2.5 g; 10.6 mmol) in anhydrous ether (20 ml) is injected dropwise into lithium aluminium hydride (401 mg; 10.6 mmol; 1 eq.) at 0° C. Stirring is then maintained for 1 hour at room temperature. At 0° C., the complex formed is hydrolysed by the successive addition of 0.32 ml of water, 0.32 ml of a 15% sodium hydroxide solution and 0.96 ml of water. The heterogeneous mixture is stirred vigorously for 1 hour. The salts having precipitated, excess water is removed using magnesium sulphate. The solid residues are filtered off; the puLe product after concentration has the appearance of a colourless oil.

Step B: 3-[(2,3-Dihydm-1,4-benzodioxin-5-yl)propyl] 4-methyl-1-benzenesulphonate The alcohol obtained in Step A (800 mg; 4.12 mmol) is dissolved in a dichloromethane/triethylamine mixture (20 ml/1.15 ml; 8.24 mmol; 2 eq.), and then tosyl chloride (1.57 g; 8.24 mmol; 2 eq.) is added. The tosylation is complete after 12 hours' stirring at room temperature. After hydrolysis, excess reagent and base are removed by extraction with dichloromethane. The purified organic phase is concentrated by chromatography over silica gel using a binary eluant AcOEt/PE (3:7). The tosylated product has the appearance of a colourless oil.

Preparation 4: 3-(2,3-Dihydro-1,4-benzodioxin-5-yl)cyanopropane

Displacement of the tosyl group of the compound obtained in Preparation 3 (2 g; 5.74 mmol) is carried out in dimethylformamide at a temperature of 100° C. for 5 hours 30 minutes in the presence of potassium cyanide (448 mg; 6.89 mmol; 1.2 eq.). After gentle hydrolysis at room temperature, the solvent is removed under reduced pressure and then the product is extracted with dichloromethane. Purification of the concentrated organic phase over a silica column, AcOEt/PE (3:7), yields the title compound in the form of a yellow oil.

Preparation 5: 3-(1,4-Benzodioxin-5-yl)propylamine

Step A: 5-Carboxy-2,3-dihydro-1,4-benzodioxin

A mixture of 10.8 g (70 mmol) of 2,3-dihydroxybenzoic acid, 38.6 g (280 mmol) of dry potassium carbonate and 24 ml (278 mmol) of 1,2-dibromoethane in 40 ml of N,N- dimethylformamide is heated at 65° C. for 24 hours under an inert atmosphere. After cooling, the reaction mixture is diluted with water and then extracted with ether. The aqueous phase is then acidified with a 3N hydrochloric acid solution and subsequently extracted with dichloromethane. After removal of the solvent by evaporation in vacuo, the residue obtained is recrystallised from toluene to yield the title acid in the form of a white solid.

Melting point 193–194° C.

Step B 5-Methoxycarbonyl-2,3-dihydro-1,4-benzodioxin 3.46 g (19.2 mmol) of the acid obtained in Step A are added to a mixture of 9.62 g (114.6 mmol) of sodium hydrogen carbonate and 3.57 ml (57.6 mmol) of iodomethanie in 40 ml of N,N-dimethylacetamide. After 24 hours' stirling under argon and protected from light, the solvent is removed by evaporation in vacuo. The residue obtained is then taken up in a 1/1 water/ethyl acetate mixture and the aqueous phase is subsequently extracted with ethyl acetate. After drying over magnesium sulphate and filtration, the solvent is removed by evaporation under reduced pressure. The title ester is obtained pure in the form of a white solid after chromatography over silica gel (eluant:AcOEt/PE:25/75).

Melting point: 59° C.

Step C: 5-Methoxycarbonyl-1,4-benzodioxin 2.58 g (13.3 mmol) of the ester obtained in Step B and 5.90 g (33.8 mmol) of N-bromosuccinimide dissolved in 40 ml of anhydrous carbon tetrachloride are heated at reflux after the addition of a spatula tip of AIBN. After 9 hours, the mixture is allowed to cool and then the succinimide formed is filtered off. The filtrate is concentrated under reduced pressure to give a quantitative yield of the dibrominated ester. The ester is subsequently taken up in 40 ml of anhydrous acetone, and then 7 g of sodium iodide (46.5 mmol) are added to the solution. After 4 days' stirrings at room temperature under an inert atmosphere, the solvent is removed by evaporation in vacuo and the residue obtained is subsequently taken up in a 1/1 water/ethyl acetate mixture. The aqueous phase is extracted with ethyl acetate. The organic phases are rendered colouLless using a saturated sodium thiosulphate solution and then dried over magnesium sulphate. After removal of the solvent by evaporation under reduced pressure and after passage over a silica column (eluant:AcOEt/PE:15/85), the title ester is obtained pure in the form of a brown syrup in a total yield of 77%.

Step D: 5-Hydroxymethyl-1,4-benzodioxin 1.62 g (8.44 mmol) of the unsaturated ester obtained in Step C are added to a suspension of 0.64 g (16.84 mmol) of lithium aluminium hydride in 40 ml of anhydrous ether. The mixture is then heated at reflux for 30 minutes under an inert atmosphere and subsequently allowed to cool. The solution is hydrolysed with, in succession, 0.64 ml of water, 0.64 ml of a 15% sodium hydroxide solution and finally 1.92 ml of water. After 30 minutes' stirring, the salts are filtered off and then the filtrate is concentrated under reduced pressure. The title alcohol is obtained pure in the form of a white solid after chromatography over silica gel (eluant:AcOEt/PE:40/60).

Melting point: 57° C.

Step E: 5-Formyl-1,4-benzodioxin

A solution of 1.27 g (10.05 mmol) of oxalyl chloride in 30 ml of anhydrous dichloromethane is cooled to −60° C. and then 1.57 g (20.1 mmol) of dimethyl sulphoxide are added to the mixture. After 5 minutes' stirring under an inert atmosphere, 1.1 g of 5-hydroxymethyl-1,4-benzodioxin (6.7 mmol) dissolved in 15 ml of dichloromethane are slowly added to the mixture which is then stirred for a further 15 minutes. 4.66 ml (33.5 mmol) of triethylamine are subsequently added to the mixture which is then allowed to return to room temperature. The solution is then acidified with a 1N hydrochloric acid solution and the aqueous phase is subsequently extracted with dichloromethane. The organic phase, dried over magnesium sulphate and then filtered, is concentrated under reduced pressure. The title aldehyde is obtained pure in the form of a yellow solid after passage over a silica column (eluant:AcOEt/PE:10/90).

Melting point: 54° C.

Step F: (E+Z)-3-(1,4-Benzodioxin-5-yl)acrylonitrile 1.11 ml (6.87 mmol) of diethyl cyanomethylphosphonate are added to a suspension of 0.28 g (6.9 mmol, at 60%) of sodium hydride in 20 ml of anhydrous tetrahydrofuran that has previously been cooled to 0° C. After 10 minutes' stirring under argon, the temperature is lowered to −78° C. and then 0.97 g (6 mmol) of 5-formyl-1,4-benzodioxin dissolved in 20 ml of anhydrous tetrahydrofuran is slowly added to the reaction mixture. After 90 minutes at −78° C. the mixture is allowed to return to room temperature and then hydrolysed with a saturated sodium hydrogen carbonate solution. The aqueous phase is extracted with ethyl acetate and then the organic phase is dried over magnesium sulphate. The solvent is subsequently evaporated off under reduced pressure and the residue obtained is then purified over a silica column (eluant:AcOEt/PE:30/70) to yield the title nitrile in the form of a yellow solid.

Melting point: 102–103° C.

Step G: 3-(1,4-Benzodioxin-5-yl)propylamine 0.925 g (5 mmol) of the nitrile obtained in Step F is dissolved in 40 ml of anhydrous ether and then 0.76 g (20 mmol) of lithium aluminium hydride is added in several portions to the reaction mixture. The reaction mixture is heated at reflux for 5 hours under argon and then allowed to return to room temperature. Hydrolysis is then carried out according to customary procedure. After filtering off the salts and removal of the solvent by evaporation in vacuo, the title amine is obtained pulre in the form of a yellow oil.

Preparation 6: 5-Hydroxy-2,3-dihydro-1,4-benzodioxin

Step A: 5-Methoxy-2,3-dihydro-1,4-benzodioxin

The procedure is as for Step A of Preparation 1. The cyclised compound is purified over a flash silica coluimn eluted with a 2:8 AcOEt/PE mixture. Yellow oil.

Step B: 5-Hydroxy-2,3-dihydro-1,4-benzodioxin

At a temperature of −10° C., boron tribromide (11.34 ml; 120 mmol; 2 eq.) is slowly injected into an anhydrous mixture of the compound obtained in Step A (10 g; 60 mmol) in dichloromethane (100 ml). The mixture is stirred for 2 hours 30 minutes. Hydrolysis is carried out at 0° C. with a saturated sodium hydirogen carbonate solution; the product is extracted at a pH of 8. The organic phase, dried over magnesium sulphate, is concentrated and then purified by flash chromatography, the binary eluant being composed of ethyl acetate and petroleum ether in a ratio of 3:7. Yellow oil.

Preparation 7: 2-(2,3-Dihydro-1,4-benzodioxin-5-yloxy)ethylamine

Step A: 5-(2-Bromoethoxy)-2,3-dihydro-1,4-benzodioxin

Dry potassium carbonate (10 eq.) is added to a solution in toluene (100 ml) of the phenolic compound obtained in Preparation 6 (2 g). After 30 minutes' heating at reflux, dibromoethane (5 eq.) and also the phase transfer agent, tetrabutylammonium bromide (0.2 eq.), are added. After refluxing for 24 hours, the salts are filtered off over Celite and the toluene is removed under reduced pressure. The compound obtained is extracted with dichloromethane in a slightly basic medium (5% sodium hydroxide solution). The concentrated organic phase is purified over a normal silica column eluted with a 3:7 AcOEt/PE mixture.

Melting point: 85° C.

Step B: 2-[2-(2,3-Dihydro-1,4-benzodioxin-5-yloxy)ethyl]isoindole-1,3-dione

Replacement of the bromine of the compound obtained in Step A is carried out in dimethylformamide (10 ml) under an argon atmosphere in the presence of potassium phthalimide (1.5 eq.) catalysed by potassium iodide (0.07 eq.). The reaction mixture is stirred and heated at reflux for 3 hours. The residual and resulting salts are removed by filtration; the product is then precipitated in the cold by the addition of water to the filtrate. The solid formed is filtered and then dried in vacuo in the presence of phosphorus pentoxide.

Melting point: 156° C.

Step C: 2-(2,3-Dihydro-1,4-benzodioxin-5-yloxy)ethylamine

Cleavage of the phthalimide group of the compound obtained in Step B is carried out in ethanol in the presence of an aqueous 98% hydrazine hydrate solution (2 eq. per 1.5 g of product). It is preferable to add the latter after 10 minutes' refluxing. When the reaction is complete, the alcohol is removed under reduced pressure. The dry residue is taken up in dichloromethane in the cold in order to precipitate the phthalic hydrazide that has formed. The latter may then be removed by filtration and the recovered and concentrated filtrate is washed several times to obtain the pule product by thin-layer chromatography.

Melting point: 65° C.

Preparation 8: 8-(2-Bromoethoxy)-3,4-dihydro-2H-1-benzothiopyran

Tetrabutylammonium bromide (1.94 g 6 mmol; 0.2 eq.), phase-transfer agent, is added to a heterogeneous mixture composed of 8-hydroxy-3,4-dihydro-2H-1-benzothiopyran (5 g; 30 mmol), acetonitrile (30 ml) and a 1.6N sodium hydroxide solution (28.3 ml; 45 mmol; 1.5 eq.). Dibromoethane (10 ml; 60 mmol; 1.5 eq.) is added after 30 minutes' stirring, the stirring being continued for 24 hours at 30° C. Concentration of the various phases under reduced pressure at 25° C. is followed by extraction of the products with dichloromethane. Washing with a 5% sodium hydroxide solution allows a first purification, which is followed by purification over a silica column eluted with a 3:7 AcOEt/PE mixture, yielding the brominated title compound.

Melting point: 62° C.

Preparation 9: 5-(3-Bromopropyl)-2,3-dihydro-1,4-benzoxathiine

A decimolar solution of the 8-(2-bromoethoxy)-3,4-dihydro-2H-1-benzothiopyran obtained in Preparation 8 (546 mg) in 20 ml of acetonitrile is heated at reflux for 48 hours. Once the solvent is removed, the crude reaction mixture is purified over a silica column eluted with a PE/CH$_2$Cl$_2$ gradient going progressively to a 2:1 mixture. The title product is obtained pure in the form of a colourless oil.

Preparation 10: 5-(3-Cyanopropyl)-2,3-dihydro-1,4-benzoxathiine

Replacement of the bromine of the compound of Preparation 9 (200 mg) using potassium cyanide (1.1 eq. to begin with) is carried out at room temperature in dimethylformamide (5 ml) under an inert atmosphere. After 12 hours' stirring, a similar addition of reagent (1.1 eq.) allows the substitution to be restarted. After hydrolysis, the solvent is removed under reduced pressure. The product is extracted with dichloromethane: the resulting concentrate of the organic phases is purified over silica gel eluted with a 3:7 AcOEt/PE mixture. Colourless oil.

Preparation 11: 4-(2,3-Dihydro-1,4-benzoxathiin-5-yl)butanoic acid

The cyano compound obtained in Preparation 10 dissolved in ethanol (10 ml) is rendered alkaline with 10% sodium hydroxide solution (5 eq.) over a period of 24 hours at 60° C. The alcohol is completely removed in vacuo, residual traces of substrates being extracted with ethyl acetate. The acid is precipitated by acidification (2N hydrochloric acid solution) of the aqueous phase, filtration of the latter yielding the pure product with the water being removed by drying in vacuo in the presence of phosphorus pentoxide.

Melting point: 93° C.

Preparation 12: 3-(2,3-Dihydro-1,4-benzoxathiin-5-yl)propanal

Step A: 5-(3-Acetoxypropyl)-2,3-dihydro-1,4-benzoxathiine

Mercuric acetate (1.17 g; 3.66 mmol; 1 eq.) is introduced into a solution of the brominated compound obtained in Preparation 9 (1 g; 3.66 mmol) in glacial acetic acid (20 ml). With the solvent at retlux, heating is maintained for 4 hours. The concentrated reaction mixture is taken up in ethyl acetate for the purpose of filtration to allow removal of the salts. The filtrate may then be extracted and subsequently washed with a saturated sodium hydrogen carbonate solution. The concentrated organic phase is purified over a silica column, AcOEt/PE (1:3). The last traces of reagent are removed by washing with a binary mixture of dichloromethane/cyclohexane (1:1); the pure ester is a yellow oil.

Step B: 3-(2,3-Dihydro-1,4-benzoxathiin-5-yl)propanol

Cleavage of the ester obtained in Step A (1.2 g; 4.75 mmol) is carried out with potassium carbonate (986 mg; 7.13 mmol; 1.5 eq.) in a MeOH/H$_2$O (48 ml; 12 ml) mixture. The acetate group is cleaved after stirring for 2 hours 30 minutes at room temperature. The salts are filtered off, the solvents are concentrated and the product is extracted with ethyl acetate. Filtration of the residual oil over a flash silica column (CH$_2$Cl$_2$ 100%) allows isolation of the compound in the form of a yellow oil.

Step C: 3-(2,3-Dihydro-1,4-benzoxathiin-5-yl)propanal

A solution of oxalyl chloride (0.68 ml: 7.85 mmol; 1.1 eq.) in anhydrous dichloromethane (18.8 ml) is prepared under argon. There is added to the latter distilled dimethyl sulphoxide in 3.7 ml of dichloromethane at −50° C. The reaction mixture is left for 2 minutes and then the alcohol obtained in Step B (1.5 g; 7.13 mmol) dissolved in 7.5 ml of dichloromethane is slowly transferred. After 30 minutes, distilled triethylamine (4.97 ml; 35.7 mmol; 5 eq.) is added in the cold. The temperature is gently raised again after 10 minutes, after which stirring is maintained for 2 hours. The product is extracted with dichloromethane, washed vigorously with water and then with a saturated sodium chloride solution. The crude oil, purified over a silica columnn, AcOEt/PE (3:7), is obtained in the pure state in a yellow colour.

EXAMPLE 1: N-[(2,3-Dihydro-1,4-benzodioxin-5-yl)methyl]acetamide

Step A: 2-[(2,3-Dihydro-1,4-benzodioxin-5-yl)methyl]isoindole-1,3-dione

The procedure is as in Step B of Preparation 7, starting from the product of Preparation 1.

Melting point: 204° C.

Step B: N-[(2,3-Dihydro-1,4-benzodioxin-5-yl)methyl]methanamine

The procedure is as in Step C of Preparation 7, starting from the compound obtained in Step A. Yellow oil.

Step C: N-[(2,3-Dihydro-1,4-benzodioxin-5-yl)methyl]acetamide

The amnine obtained in Step B is dissolved in pyridine (5 ml) under an argon atmosphere, and acetic anhydride (1.2 eq.) is added at 0° C. Stirring is carried out at room temperature for 2 hours, after which acetylation is complete. The solvent is removed under reduced pressure and the reaction mixture is then extracted with dichloromethane. The organic phase is washed with water, dried over magnesium sulphate and then concentrated. The product so obtained is dried in vacuo in order to eliminate residual traces of pyridine before purification; the latter is carried out by flash chromatography using an eluant composed of a 7:3 $CHCl_3$/AcOEt mixture.

Melting point: 18° C.

EXAMPLE 2: N-[(2,3-Dihydro-1,4-benzodioxin-5-yl)methyl]-N-methylacetamide

The title compound is obtained by conventional alkylation with dimethyl sulphate, in basic medium, of the compound obtained in Example 1.

EXAMPLE 3: N-[2-(2,3-Dihydro-1,4-benzodioxin-5-yl)ethyl]acetamide

Step A: 5-Cyanomethyl-2,3-dihydro-1,4-benzodioxin

The procedure is as for Preparation 10, starting from the compound of Preparation 1. Purification is carried out using a 1:9 AcOEt/PE mixture.

Melting point 47° C.

Step B: 2-(2,3-Dihydro-1,4-benzodioxin-5-yl)ethylamine

A solution of the cyano compound obtained in Step A (1.5 g 8.37 mmol) in anhydrous ether (25 ml) is added to lithium aluminium hydride (635 mg; 16.7 mmol; 2 eq.) at 0° C. The whole is then heated at retlux for 4 hours. After cooling, the complex is hydrolysed in succession with 0.63 ml of water, 0.63 ml of 15% sodium hydroxide solution and 1.89 ml of water. The alumina salts finally precipitate at the end of one hour's stirring. Aqueous traces are removed by magnesium sulphate added to the reaction mixture. The filtrate obtained by filtration is then concentrated, yielding the pure amine in the form of a yellow oil.

Step C: N-[2-(2,3-Dihydro-1,4-benzodioxin-5-yl)ethyl]acetamide

The procedure is as in Step C of Example 1, starting from the compound obtained in Step B.

Melting point 57° C.

EXAMPLE 4: N-Methyl-[3-(2,3-dihydro-1,4-benzodioxin-5-yl)]propanamide

Step A: 3-(2,3-dihydro-1,4-benzodioxin-5-yl)propanoic acid

A 10% sodium hydroxide solution (2 eq.) is introduced under an argon atmosphere into a reaction mixture comprising the ester obtained in Preparation 2 dissolved in ethanol (10 to 15 ml). After 2 hours' heating at reflux, extraction is carried out with ethyl acetate. Acidification of the aqueous phase in the cold with a 2N then a 3N hydrochloric acid solution causes precipitation of the expected product. The product is filtered off and then dried in vacuo in the presence of phosphorus pentoxide.

Melting point: 73° C.

Step B: N-Methyl-[3-(2.3-dilhydro-1,4-benzodioxin-5-yl)]propanamide

Coupling agyents, such as hydroxybenzotriazole (1.1 eq.), and 1-(3-dimethylaminopropyl)-3-ethylcarbodiimide hydrochloride (1.1 eq.), are introduced at 0° C., under an inert atmosphere, into a reaction mixture comprising the acid obtained in Step A dissolved in anhydrous dimethylformamide (10 ml). The argon circulation being discontinued, a 10% solution of methylamine in benzene (1.5 eq.) can then be added. The temperature is very slowly brought to 20° C. and stirring is maintained for 18 hours. Evaporation of the solvent allows extraction of the product with dichloroinethaiie, washing with water removing excess reagents. The dried, concentrated organic phase is puiified by tlash chromatography eluted with a 7:3 $CHCl_3$/AcOEt mixture.

Melting point: 99° C.

EXAMPLE 5: N-Methyl-[3-(2,3-Dihydro-1,4-benzodioxin-5-yl)]propanethioamide

The title compound is obtained by the action of Lawesson's reagent on the compound obtained in Example 4.

EXAMPLE 6: N-[4-(2,3-Dihydro-1,4-benzodioxin-5-yl)butyl]acetamide

Step A: 4-(2,3-Dihydro-1,4-benzodioxin-5-yl)butylamine

The procedure is as in Step B of Example 3 starting from the compound of Preparation 4.

Step B: N-[4-(2,3-Dihydro-1,4-benzodioxin-5-yl)butyl]acetamide

The procedure is as in Step C of Example 3, starting from the compound obtained in Step A. Yellow gum.

EXAMPLE 7: N-[4-(2,3-Dihydro-1,4-benzodioxin-5-yl)butyl]-3-butenaniide

By proceeding as in Example 6 using the appropriate anhydride in Step B, the compound of Example 7 is obtained.

EXAMPLE 8: N-[3-(2,3-Dihydro-1,4-benzodioxin-5-yl)propyl]acetamide

Step A: 5-(3-Azidopropyl)-2,3-dihydro-1,4-benzodioxin

Displacement of the tosyl group of the compound obtained in Preparation 3 (1 g; 2.87 mmol) is carried out in dimethylformamide (30 ml) in the presence of sodium azide (560 mg; 8.61 mmol; 3 eq.). The reaction is complete after 12 hours' stirring at room temperature. The solvent is removed and the product is then extracted with dichloromethane, washed with water and subsequently purified over a silica column eluted with a 3:7 AcOEt/PE mixture. The desired azide is obtained in the form of a colourless oil.

Step B: N-[3-(2,3-Dihydro-1,4-benzodioxin-5-yl)propyl]acetamide

The amine is first of all synthesised by catalytic hydrogenation of the compound obtained in Step A. The latter (900 mg; 4.1 mmol) is dissolved with ethanol (15 ml) in the reactor of a Paar apparatus. After the addition of the catalyst, in this case 10% palladium on carbon (90 mg; 10% by weight), stirring is maintained for 4 hours at room temperature at a hydrogen pressure of 45 psi. The reaction mixture is filtered and then concentrated under reduced pressure, and the amine is recovered in the form of a colourless oil. The latter is of the correct purity according to thin-layer chromatography and will thus be acetylated directly under the conditions of Step C of Example 1. Pale yellow oil.

EXAMPLE 9: N-[3-(2,3-Dihydro-1,4-benzodioxin-5-yl)propyl]-2-phenylacetamide

The procedure is as in Example 8, with replacement of the acetic anhydride with phenylacetic anhydride.

Similarly, the compound of Example 10 is obtained by replacing the acetic anhydride with cyclohexanecarboxylic anhydride:

EXAMPLE 10: N-[3-(2,3-Dihydro-1,4-benzodioxin-5-yl)propyl]cyclohexanecarboxamide

EXAMPLE 11: N-Methyl-[4-(2,3-dihydro-1,4-benzodioxin-5-yl)]butanamide

Step A: 4-(2,3-dihydro-1,4-benzodioxin-5-yl)butanoic acid

The procedure is the same as in Preparation 11, starting from the compound obtained in Preparation 4.
Melting point: 54° C.

Step B: N-Methyl-[4-(2,3-dihydro-1,4-benzodioxin-5-yl)]butanamide

The procedure is as in Step B of Example 4, starting from 4-(2,3-dihydro-1,4-benzodioxin-5yl)-butanoic acid.
Melting point: 79° C.

| Elemental microanalysis: | C | H | N |
|---|---|---|---|
| % Calculated | 66.36 | 7.28 | 5.95 |
| % Found | 66.31 | 7.21 | 5.95 |

EXAMPLE 12: N-Cyclobutyl-4-(2,3-Dihydro-1,4-benzodioxin-5-yl)butanamide

The procedure is as in Example 11, with replacement of the methylamine with cyclobutylamine.

EXAMPLE 13: N-Methyl-[5-(2,3-dihydro-1,4-benzodioxin-5-yl)]pentanamide

Step A: 3-(2,3-Dihydro-1,4-benzodioxin-5-yl)propanal

Diisobutylaluminium hydride (1M) (3.43 ml; 3.43 mmol; 0.9 eq.) is slowly injected at −78° C. into a solution of the ester obtained in Preparation 2 dissolved in toluene. After 45 minutes' stirring at the same temperature, hydrolysis is carried out with 2N hydrochloric acid. At 20–25° C., the products are extracted with AcOEt and then purified over a silica column eluted with a 2:8 AcOEt/PE mixture. The compound, collected in the form of a colourless oil, corresponds to the aldehyde.

Step B: 5-(4-Ethoxycarbonylbut-3-ene)-2,3-dihydro-1,4-benzodioxin

The procedure is as in Step B of Preparation 2, startin from the compound obtained in Step A. Colourless oil.

Step C: Ethyl 5-(2,3-dihydro-1,4-benzodioxin-5-yl) pentanoate

Catalytic hydrogenation of the unsaturation of the ester obtained in Step B (600 mg; 2.29 mmol) yields a colourless oil having the butyl chain characteristic of the desired compound.

Step D: 5-(2,3-Dihydro-1,4-benzodioxin-5-yl)pentanoic acid

The procedure is as in Step A of Example 4, starting from the ester obtained in Step C.
Melting point: 56° C.

Step E: N-Methyl-[5-(2,3-dihydro-1,4-benzodioxin-5-yl)] pentanamide

The procedure is as in Step B of Example 4, starting from the acid obtained in Step D.
Melting point: 79° C.

| Elemental microanalysis: | C | H | N |
|---|---|---|---|
| % Calculated | 67.45 | 7.68 | 5.62 |
| % Found | 67.50 | 7.70 | 5.41 |

EXAMPLE 14: N-Benzyl-5-(2,3-dihydro-1,4-benzodioxin-5-yl)pentanamide

The procedure is as in Example 13, with replacement of the N-methylamine with N-benzylamine.

EXAMPLE 15: N-[3-(1,4-Benzodioxin-5-yl)propyl] acetamide

A solution of 0.885 g (4.63 mmol) of the amine obtained in Preparation 5 in 10 ml of anhydrous pyiidine is cooled to 0° C. and then 0.53 ml (5.56 mmol) of acetic anhydride is added to the mixture. After one hour's stirring at 0° C. under an inert atmosphere, the mixture is diluted with ethyl acetate and then the organic phase is acidified with a 1N hydrochloric acid solution. After extraction of the aqueous phase with ethyl acetate, the organic phases are dried over magnesium sulphate and then concentrated under reduced pressure. The residue obtained is purified over a silica column (eluant:methanol/dichloromethane 3:97) to yield the title amide in the form of a clear syrup.

EXAMPLE 16: N-[3-(3-Methyl-1,4-benzodioxin-5-yl)propyl]acetamide

EXAMPLE 17: N-[3-(3-Benzyl-1,4-benzodioxin-5-yl)propyl]acetamide

Examples 16 and 17 are obtained as follows:

After protection of the amine obtained in Preparation 5 in the form of dibenzylamine, the introduction of lithium is carried out using lithium diisopropylamide, which is followed by condensation of the desired electrophile. After debenzylation by catalytic hydrogenation, and acetylation in accordance with the procedure used in Step C of Example 1, the title compounds are obtained.

EXAMPLE 18: N-[3-(3-Methyl-2,3-dihydro-1,4-benzodioxin-5-yl)propyl]acetamide The procedure is as for Example 16 using stronger pressure and temperature conditions for the catalytic hydrogenation.

EXAMPLE 19: N-[3-(1,4-Benzodioxin-5-yl)propyl] butanamide

A solution of 1 g (5.23 mmol) of the amine obtained in Preparation 5 in 20 ml of anhydrous dichloromethane is cooled to 0° C. and then 0.78 g (7.32 mmol) of butyryl chloride and 1.58 g (15.7 mmol) of triethylamine are added in succession to the mixture. After 30 minutes' stirring, the reaction mixture is acidified with a 1N hydrochloric acid solution. After extraction with dichloromethane, the organic phases are dried over magnesium sulphate and then concentrated in vacuo. The residue obtained is purified over a silica column (eluant:petroleum ether/ethyl acetate 50:50) to yield the title amide in the form of a thick oil.

EXAMPLE 20: N-[2-(2,3-Dihydro-1,4-benzodioxin-5-yloxy)ethyl]acetamide

The procedure used is the same as that in Step C of Example 1, starting from the compound of Preparation 7.

EXAMPLE 21: N-[2-(2,3-Dihydro-1,4-benzodioxin-5-yloxy)ethyl]-2-phenylacetamide The procedure is as in Example 20, with replacement of the acetic anhydride with phenylacetic anhydride.

EXAMPLE 22: N-[2-(2,3 Dihydro-1,4-benzodioxin-5-yloxy)ethyl]cyclopropanecarboxamide Cyclopropanoyl chloride (0.74 ml; 8.2 mmol; 1.6 eq.) is slowly introduced into a reaction mixture comprising the amine obtained in Preparation 7 (1 g; 5.1 mmol) dissolved in a dichloromethane/triethylamine (20 ml; 9.28 ml; 67 mmol: 13 eq.) mixture. This operation is carried out at 0° C., and then the reaction mixture is gently brought to room temperature over a period of 2 hours' stirring. Excess reagent and and excess base are removed by washing with water during extraction with dichloromethane. The dried, concentrated organic phase results in an orange solid, which is purified over a silica column ($CH_2Cl_2$/MeOH:2%) and then recrystallised from a binary mixture of diethyl ether and acetonitrile.

Melting point: 137° C.

EXAMPLE 23: N-[2-(2,3-Dihydro-1,4-benzodioxin-5-yloxy)ethyl]-N'-propylurea

After dissolution of the amine obtained in Preparation 7 (800 mg; 4.1 mmol) in toluene under an argon atmosphere, n-propyl isocyanate (0.58 ml; 6.15 mmol; 1.5 eq.) is added at 0° C. The reaction mixture is stirred at room temperature for 2 hours. Excess reagent is then neutralised by hydrolysis, and the removal of the solvent under reduced pressure yields a mixture which is extracted with dichloromethane. Purification is effected over a silica column eluted with a $CH_2Cl_2$/MeOH 2% mixture and by washing with diethyl ether.

Melting point: 164° C.

EXAMPLE 24: N-[2-(2,3-Dihydro-1,4-benzodioxin-5-yl)ethyl]-N'-propylurea

The procedure is as in Example 23, starting from the amine obtained in Step B of Example 3.

EXAMPLE 25: N-[4(2,3-Dihydro-1,4-benzodioxin-5-yloxy)butyl]acetamide

Step A: 5-(4-Bromobutoxy)-2,3-dihydro-1,4-benzodioxin

The procedure used is the same as that in Step A of Preparation 7, starting from the compound of Preparation 6.

Melting point: 42° C.

Step B: 2-[4-(2,3-Dihydro-1,4-benzodioxin-5-yloxy)butyl]isoindole-1,3-dione

The procedure used is the same as that in Step B of Preparation 7, starting from the compound obtained in Step A.

Melting point: 112° C.

Step C: 4-(2,3-Dihydro-1,4-benzodioxin-5-yloxy)butylamine

The procedure used is the same as that in Step C of Preparation 7, starting from the compound obtained in Step B. Yellow oil.

Step D: N-[4-(2,3-Dihydro-1,4-benzodioxin-5-yloxy)butyl]acetamide

The procedure used is the same as that in Step C of Example 1, starting from the compound obtained in Step C.

Melting point: 91° C.

| Elemental microanalysis: | C | H | N |
|---|---|---|---|
| % Calculated | 63.38 | 7.22 | 5.28 |
| % Found | 63.20 | 7.22 | 5.30 |

The compound of Example 26 is obtained in an analogous manner to Example 25.

EXAMPLE 26: N-[3-(2,3-Dihydro-1,4-benzodioxin-5-yloxy)propyl]acetamide

Step A: 5-(3-Bromopropoxy)-2,3-dihydro-1,4-benzodioxin

Melting point: 54° C.

Step B: 2-[3-(2,3-Dihydro-1,4-benzodioxin-5-yloxy)propyl]isoindole-1,3-dione

Melting point: 128° C.

Step C: 3-(2,3-Dihydro-1,4-benzodioxin-5-yloxy)propylamine

Melting point: 134° C.

Step D: N-[3-(2,3-Dihydro-1,4-benzodioxin-5-yloxy)propyl]acetamide

Melting point: 96° C.

EXAMPLE 27: N-[3-(2,3-Dihydro-1,4-benzodioxin-5-yloxy)propyl]ethanethioamide The title product is obtained by treating the compound obtained in Example 26 with Lawesson's reagent.

EXAMPLE 28: N-Methyl-[3-(4,4-dioxo-2,3-dihydro-1,4-benzoxathiin-5-yl)]propanamide Step A: 3-(4,4-dioxo-2,3-dihydro-1,4-benzoxathiin-5-yl)propanoic acid 150 mg of the compound obtained in Preparation 12 are dissolved in tert-butanol (5 ml) and a molar solution of potassium permanganate (4.32 ml; 4.32 mmol; 6 eq.) and also a 0.16M hydrogen phosphate buffer solution (0.9 ml; 0.144 mmol; 0.2 eq.) are introduced. After 40 minutes' stirring at room temperature, excess potassium pelmanganate is treated with a saturated sodium sulphite solution. The manganese oxide formed is filtered off and the concentrated filtrate is extracted with dichloromethane. Precipitation of the aqueous phase from acidic medium yields the acid.

Step B: N-Methyl-[3-(4,4-dioxo-2,3-dihydro-1,4-benzoxathiin-5-yl)]propanamide

The procedure used is the same as that in Step B of Example 4, starting from the acid obtained in Step A.

Melting point: 157° C.

| Elemental microanalysis: | C | H | N | S |
|---|---|---|---|---|
| % Calculated | 53.52 | 5.61 | 5.20 | 11.91 |
| % Found | 53.56 | 5.57 | 5.27 | 11.91 |

EXAMPLE 29: N-[5-(2,3-dihydro-1,4-benzoxathiin-5-yl)pentyl]acetamide

Step A: 5-(4-Cyanobut-3-ene)-2,3-dihydro-1,4-benzoxathiine

The procedure is as in Step F of Preparation 5, starting from the compound obtained in Preparation 12. Yellow oil.

Step B: 5-(4-Cyanobutyl)-2,3-dihydro-1 4-benzoxathiine

The compound obtained in Step A is reduced according to the procedure in Step C of Preparation 2. Colourless oil.

Step C: N-[5-(2,3-dihydro-1,4-benzoxathiin-5-yl)pentyl]acetamide

The saturated cyano compound obtained in Step B (400 mg 1.71 mmol) is dissolved in the reactor of a Paar apparatus using acetic anhydride. Sodium acetate (211 mg; 2.57 mmol; 1.5 eq.) and Raney nickel (48 mg) are then introduced into the reaction mixture. The whole is heated at 50° C. under an initial hydrogen pressure of 40 psi for 12 hours. The solvent is removed after returning to normal temperature and pressure conditions, and the product is then extracted with ethyl acetate. Purification of the concentrated organic phase by flash chromatography, CHCl₃/AcOEt (7:3), yields the title amide, which precipitates in the cold and is washed with diethyl ether.

Melting point: 93° C.

| Elemental microanalysis: | C | H | N | S |
|---|---|---|---|---|
| % Calculated | 64.48 | 7.58 | 5.01 | 11.48 |
| % Found | 64.62 | 7.67 | 5.09 | 11.19 |

EXAMPLE 30: N-[3-(2,3-Dihydro-1,4-benzoxathiin-5-yl)propyl]acetamide

Step A: 2-[3-(2,3-Dihydro-1,4-benzoxathiin-5-yl)propyl]isoindole-1,3-dione

The procedure is as in Step B of Preparation 7, starting from the compound of Preparation 9.

Melting point: 132° C.

Step B: 3-(2,3-Dihydro-1,4-benzoxathiin-5-yl)propylamine

The procedure is as in Step C of Preparation 7, starting from the compound obtained in Step A. Yellow oil.

Step C: N-[3-(2,3-Dihydro-1,4-benzoxathiin-5-yl)propyl]acetamide

The procedure is as in Step C of Example 1, starting from the compound obtained in Step B. Yellow gum.

EXAMPLE 31: N-[3-(2,3-Dihydro-1,4-benzoxathiin-5-yl)propyl]cyclopropanecarboxamide The procedure is as in Example 30. with replacement of the acetic anhydride in Step C with cyclopropanecarboxylic anhydride.

EXAMPLE 32: N-[3-(2,3-Dihydro-1,4-benzoxathiin-5-yl )propyl]-N'-propylurea

The procedure is as in Example 23, starting fomm the amine obtained in Step B of Example 30.

EXAMPLE 33: N-[4-(2,3-Dihydro-1,4-benzoxathiin-5-yl)butyl]acetamide

Step A: 4-(2,3-Dihydro-1,4-benzoxathiin-5-yl)butylamine

The procedure is as in Step B of Example 3, starting from the compound obtained in Preparation 10. Yellow oil.

Step B: N-[4-(2,3-Dihydro-1,4-benzoxathiin-5-yl)butyl]acetamide

The procedure is as in Step C of Example 1, starting from the compound obtained in Step A. Yellow gum.

EXAMPLE 34: N-[2-(3,4-Dihydro-2H-1-benzothiopyran-8-yloxy)ethyl]acetamide

Step A: 2-[2-(2H-1-Benzothiopyran-8-yloxy)ethyl]isoindole-1,3-dione

The procedure is as in Step A of Example 1, starting from the compound of Preparation 8.

Melting point: 154° C.

Step B: 2-(3,4-Dihydro-2H-1-benzothiopyran-8-yloxy)ethylamine

The procedure is as in Step B of Example 1, starting from the compound obtained in Step A.

Melting point: 45° C.

Step C: N-[2-(3.4-Dihydro-2H-1-benzothiopyran-8-yloxy)ethyl]acetamide

The procedure is as in Step C of Example 1, starting from the compound obtained in Step B.

Melting point: 117° C.

EXAMPLE 35: N-Methyl-[4-(2,3-dihydro-1,4-benzoxathiin-5-yl)]butanamnide

The procedure is as in Step B of Example 4, starting from the compound of Preparation 11.

Melting point: 94° C.

Examples 36, 37 and 38 are obtained in the same manner as in Example 35 by condensing the appropriate amine.

EXAMPLE 36: N-Allyl-4-(2,3-dihydro-1,4-benzoxathiin-5-yl)butanamide

EXAMPLE 37: N-Propyl-[4-(2,3-dihydro-1,4-benzoxathiin-5-yl)]butanamide

Melting point: 93° C.

| Elemental microanalysis: | C | H | N | S |
|---|---|---|---|---|
| % Calculated | 64.48 | 7.58 | 5.01 | 11.48 |
| % Found | 64.79 | 7.59 | 5.08 | 11.39 |

EXAMPLE 38: N-Ethyl-[4-(2,3-dihydro-1,4-benzoxathiin-5-yl)]butanamide

Melting point: 86° C.

| Elemental microanalysis: | C | H | N | S |
|---|---|---|---|---|
| % Calculated | 63.37 | 7.22 | 5.28 | 12.08 |
| % Found | 63.77 | 7.27 | 5.36 | 11.98 |

EXAMPLE 39: N-[2-(3,4-Dihydro-2H-1-benzopyran-8-yloxy)ethyl]acetamide

Step A: 1-Methoxy-2-(2-propynyloxy)benzene

Condensation of propargyl bromide (10% solution in toluene) (8.97 ml; 100.7 mmol; 1 eq.) with guaiacol (10 g; 80.5 mmol) is carried out under an argon atmosphere in acetone (150 ml) in the presence of potassium carbonate (13.36 g; 96.7 mmol; 1.2 eq.). After refluxing for 20 hours, the solvent is removed under reduced pressure following removal of the salts by filtration over Celite. On extraction of the concentrate with dichloromethane, the organic phase is washed in succession with a 5% then a 10% sodium hydroxide solution. The latter, dried over magnesiumn sulphate and then evaporated, is purified over silica el using a 3:7 AcOEt/PE mixture. The acetylenic compound is obtained in the form of a yellow oil.

Step B: 8-Methoxy-2H-1-benzopyran

Cyclisation of the acetylenic compound obtained in Step A (3 g; 18.5 mmol) requires heating at approximately 240° C. for 5 hours 30 minutes. In order to do that, the choice of a solvent such as triethylene glycol (74 ml; 555 mmol: 30 eq.) proves indispensable, and it is furthermore desirable to carry out the operation in an anhydrous medium. The reaction mixture is cooled to room temperature, and 50 ml of diethyl ether are then introduced to extract the product. After washing the organic phase 4 times in succession with a saturated sodium chloride solution, the concentrate is purified over a silica column. Elution with petroleum ether and then with a 1:9 AcOEt/PE mixture yields the chromene in the form of a yellow oil.

Step C: 8-Methoxy-3,4-dihydro-2H-1-benzopyran

The compound obtained in Step B (1 g:6.84 mmol) dissolved in glacial acetic acid (10 ml) is poured into the reactor of a Paar apparatus. 10% palladium on carbon (10% by weight; 100 mg), acting as catalyst, is added. The whole is then subjected to a hydrogen pressure of 45 psi for 12 hours at room temperature. After filtration, the solvent is removed under reduced pressure and then extraction is carried out with dichloromethane. The recovered organic phase, dried over magnesium sulphate, is purified after concentration over a silica column eluted with pure dichloromethane. The title product is obtained pure in the form of a yellow oil.

Step D: 8-Hydroxy-3,4-dihydro-2H-1-benzopyran

The compound obtained in Step C (1 g; 6.09 mmol) is dissolved in glacial acetic acid (10.2 ml) and then hydrobromic acid (48% solution in water) (3.7 eq.; 47 mmol; 2.54 ml) is added dropwise. The phenol is fully deprotected after 5 hours' reflux. After removal of the solvent under reduced pressure, the dry residue is taken up in aqueous medium and then neutralised with a saturated sodium hydrogen carbonate solution to a pH of 8. Extraction with ethyl acetate yields an orange oil after drying and concentration. After purification of the latter over a silica column. AcOEt/PE (3:7), the oil is yellow in colour.

Step E: 8-(2-Bromoethoxy)-3,4-dihydro-2H-1-benzopyran

The procedure is the same as that in Step A of Preparation 7, starting from the compound obtained in Step D.

Melting point: 70° C.

Step F: 2-[2-(2H-1-Benzopyran-8-yloxy)ethyl]isoindole-1,3-dione

The procedure is as in Step A of Example 1, starting from the compound obtained in Step E.

Melting point: 104° C.

Step G: 2-(3,4-Dihydro-2H-1-benzopyran-8-yloxy) ethylamine

The procedure is as in Step B of Example 1, starting from the compound obtained in Step F.

Step H: N-[2-(3,4-Dihydro-2H-1-benzopyran-8-yloxy) ethyl]acetamide

The procedure is as in Step C of Example 1, starting from the compound obtained in Step G.

Melting point: 111° C.

EXAMPLE 40: N-Methyl-4-(1,4-benzodioxin-5-yl) butanamide

Step A: Ethyl 3-(1,4-benzodioxin-5-yl)-2-propenoate 4.13 g (12 mmol) of ethoxycarbonylmethylenetriphenylphosphorane are added to a solution of 1.3 g (8 mmol) of the aldehyde obtained in Step E of Preparation 5 in 20 ml of toluene, and then the mixture is stirred under arson at room temperature for 2 hours. The solvent is evaporated off in vacuo and then the residue obtained is purified over a silica column (eluant:AcOEt/PE:85/15) to yield the title ester in the E configuration in the form of a yellow solid.

Melting point: 58° C.

Step B: Ethyl 3-(1,4-benzodioxin-5-yl)-2-propanoate 4.2 g (172 mmol) of magnesium are added to a solution of 1 g (4.3 mmol) of the ester obtained in Step A in 30 ml of anhydrous methanol. After cooling, the reaction mixture is stirred for 24 hours and then the salts are dissolved with a 6N hydrochloric acid solution. The aqueous phase is extracted with dichloromethanie and then the organic phase is dried over magnesium sulphate. After evaporation of the solvent in vacuo, the residue obtained is purified over a silica column (eluant:AcOEt/PE:10/90) to yield the title ester in the form of a clear oil.

Step C: 3-( 1,4-benzodioxin-5-yl)-1-propanol 233 g (6.14 mmol) of lithium aluminium hydride are added to a solution of 0.9 g (4.09 mmol) of the ester obtained in Step B in 30 ml of anhydrous ether and then the mixture is heated at reflux for 30 minutes. After cooling, the solution is hydrolysed in accordance with customary procedure and then the salts are filtered off. The filtrate is subsequently concentrated in vacuo and then the crude product is purified by chromatography over a silica column (eluant:AcOEt/PE:40:60) to yield the title alcohol in the form of a clear oil.

Step D: 3-(1,4-benzodioxin-5-yl)propyl 4-methyl-1-benzenesulphonate 1.28 g (6.72 mmol) of tosyl chloride are added to a solution of 0.86 g (4.448 mmol) of the alcohol obtained in Step C and 1.9 ml (13.44 mmol) of triethylamine in 20 ml of anhydrous dichloromethane. The mixture is stirred for 24 hours at room temperature and then the solvent is evaporated off in vacuo. The crude product is purified over a silica column (eluant:AcOEt/PE:5/95 then 10/90) to yield the title tosylate in the form of a clear syrup.

Step E: 4-(1,4-benzodioxin-5-yl)butanenitrile

A solution of 1.065 g (3.07 mol) of the tosylate obtained in Step D and 0.5 g (7.7 mmol) of potassium cyanide is heated at reflux in 15 ml of DMF for 4 hours under argon. The mixture is allowed to cool and then the solvent is evaporated off in vacuo. The residue obtained is taken up in water and then the aqueous phase is extracted with dichloromethane. After drying over magnesium sulphate, the organic phase is concentrated under reduced pressure. Chromatography over silica gel (eluant:PE/AcOEt:90/10) yields the title nitrile in the form of a clear oil.

Step F: 4-(1,4-benzodioxin-5-yl)butanoic acid 0.58 g (2.90 mmol) of the nitrile obtained in Step E in 20 ml of a 10% sodium hydroxide solution is heated at retlux for 20 hours. After evaporating off the solvent in vacuo, the salts are dissolved in 20 ml of a 1N hydrochloric acid solution. The aqueous phase is extracted with ethyl acetate and then the organic phase is diied over magnesium sulphate. Removal of the solvent by evaporation under reduced pressure yields the title acid in the form of a white solid in a quantitative yield.

Melting point 75–76° C.

Step G: N-methyl-4-( 1,4-benzodioxin-5-yl)butanamide 0.1 g (0.75 mmol) of hydroxybenzotriazole (HOBt) and 0.14 g (0.75 mmol) of 1-(3dimethylaminopropyl)-3-ethylcarbodiimide hydrochloride (EDC) are introduced at 0° C. into a reaction mixture comprising 0.15 g (0.68 mmol) of the acid obtained in Step F dissolved in 3 ml of anhydrous DMF. After the addition of 1.02 mmol of a 10% solution of methylamine in benzene, stirring is maintained for 24 hours and then the solvent is evaporated off in vacuo. The residue obtained is taken up in dichloromethane and then washed with water. The organic phase is dried over magnesium sulphate and then concentrated in vacuo. Chromatography over silica gel (eluant:AcOEt/PE:70/30) allows isolation of the title amide in the form of a clear oil.

EXAMPLE 41: N-Propyl-4-(1,4-benzodioxin-5-yl) butanamide

A suspension of 0.29 g (2.6 mmol) of n-propylamine hydrochloride in 7 ml of anhydrous N,N-dimethylformamide is cooled to 0° C. and then 0.33 g (3.54 mmol) of N,N-dimethylaminopyridine are added to the mixture. After the addition of 0.41 g (2.36 mmol) of the acid obtained in Step F of Example 40, 0.5 g (2.6 mmol) of EDC is added to the mixture. The solution is stirred for 12 hours under argon at room temperature and then the solvent is evaporated off in vacuo. The residue is taken up in a water/ethyl acetate (1/1) mixture and then the aqueous phase is extracted with ethyl acetate. The organic phase is dried over magnesium sulphate and then concentrated under reduced pressure. Chromatography over silica gel (eluant:AcOEt/PE:70/30) yields the title amide in the form of a clear syrup.

EXAMPLE 42: N-Propyl-4-(2,3-dihydro-1,4-benzodioxin-5-yl)butanamide

Propylamine hydrochloride (134 mg, 1.5 eq) is dissolved in 5 ml of DMF and placed in ice. The acid obtained in Step A of Example 11 (260 mg) dissolved in 1 ml of DMF is then added to the reaction mixture. EDC (247 mg, 1.1 eq) is then added. Stirring is maintained overnight while allowing the temperature to rise again.

The DMF is evaporated off, and then the residue is hydrolysed and extracted with ethyl acetate.

The organic phase is died over $MgSO_4$.

The product, purified by flash chlomatography (eluant:PE/AcOEt, 8/2), is obtained in the form of a white solid.

Melting point: 57–58° C.

| Elemental microanalysis: | C | H | N |
|---|---|---|---|
| % Calculated | 68.41 | 8.04 | 5.32 |
| % Found | 68.59 | 8.14 | 5.38 |

EXAMPLE 43: N-[3-(2,3-Dihydro-1,4-benzodioxin-5-yl)propyl]butanamide

The amine obtained above in Step B of Example 8 (300 mg) is dissolved in 7 ml of $CH_2Cl_2$. At 0° C. triethylamine (0.708 ml, 1.2 eq) and butanoyl chloride (0.248 ml, 1.2 eq) are added. The reaction mixture is stirred at 0° C. for 5 hours. The mixture is then acidified with 1N hydrochloric acid and subsequently extracted with $CH_2Cl_2$. The organic phase is washed with a saturated sodium hydrogen carbonate solution and then dried over $MgSO_4$.

The product, purified by flash chromatography (eluant:PE/AcOEt, 8/2), is obtained in the form of a colourless oil.

EXAMPLE 44: N-Methyl-3-(2,3-dihydro-1,4-benzoxathiin-5-yl)propanamide

Step A: 3-(2,3-dihydro-1,4-benzoxathiin-5-yl)propanoic acid

The aldehyde obtained in Preparation 12 is subjected to oxidation with silver nitrate in a basic medium (G. Guillaumet et al., Can. J. Chem. 1992, 70, 828–835) to yield the title product.

Step B: N-Methyl-3-(2,3-dihydro-1,4-benzoxathiin-5-yl)propanamide

The procedure is as in Example 42, with replacement of propylamine hydrochloride with methylamine hydrochloride.

Melting point: 98–99° C.

| Elemental microanalysis: | C | H | N | S |
|---|---|---|---|---|
| % Calculated | 60.73 | 6.37 | 5.90 | 13.51 |
| % Found | 60.46 | 6.35 | 5.75 | 13.53 |

EXAMPLE 45: N-Methyl-5-(2,3-dihydro-1,4-benzoxathiin-5-yl)pentanamide

The procedure is as in Steps B, C, D and E of Example 13, starting from the compound obtained in Preparation 12.

Melting point: 66° C.

| Elemental microanalysis: | C | H | N | S |
|---|---|---|---|---|
| % Calculated | 63.36 | 7.22 | 5.28 | 12.08 |
| % Found | 63.65 | 7.19 | 5.35 | 12.40 |

PHARMACOLOGICAL STUDY

EXAMPLE A: Acute toxicity study

The acute toxicity was evaluated after oral administration to groups each comprising 8 mice (26±2 grams). The animals were observed at regular intervals during the course of the first day, and daily for the two weeks following treatment. The $LD_{50}$ (dose that causes the death of 50% of the animals) was evaluated and demonstrated the low toxicity of the majority of the compounds of the invention.

EXAMPLE B: Melatonin receptor binding study

1) Study on pars tuberalis cells of sheep

Melatonin receptor binding studies of the compounds of the invention were carried out according to conventional techniques on pars tuberalis cells of sheep. The pars tuberalis of the adenohypophysis is in fact characterised in mammals by a high density of melatonin receptors (Journal of Neuroendocrinology, 1, pp. 1–4, 1989).

Protocol

1) Sheep pars tuberalis membranes are prepared and are used as target tissue in saturation experiments in order to determine the binding capacities and affinities for $[^{125}I]$-iodomelatonin.

2) Sheep pars tuberalis membranes are used as target tissue in competitive binding experiments using the various test compounds in comparison with melatonin.

Each experiment is canted out in triplicate and a range of different concentrations is tested for each compound. The results enable the determination, after statistical processing, of the binding affinities of the compound tested.

Results

The compounds of the invention appear to possess a strong affinity for melatonin receptors.

2) Study on membranes of chicken (*Gallus Domesticus*) brain homogenate

The animals used are 12-day-old chickens (*Gallus domesticus*). They are sacrificed on the day of their arrival after 13 to 17 hours. The brains are quickly removed and frozen at −200° C. and then stored at −80° C. The membranes are prepared according to the method described by Yuan and Pang (Journal of Endocrinology, 128, pp. 475–482, 1991). $[^{125}I]$ melatonin is incubated for 60 minutes at 25° C. in the presence of the membranes in a buffered solution of pH 7.4. At the start of that period, the membrane suspension is filtered (Whatman GF/C). The radioactivity retained on the filter is determined using a Beckman® LS 6000 liquid scintillation counter.

The products used are:

2-[$^{125}$I] melatonin melatonin current products original molecules

In primary screening, the molecules are tested at 2 concentrations ($10^{-7}$ and $10^{-5}$M). Each result is the average of 3 independent measurements. The active molecules chosen following the pnimary screening results are subjected to a quantitative determination of their efficacy ($IC_{50}$). They are used at 10 different concentrations.

The $IC_{50}$ values found for the preferred compounds of the invention, which correspond to the affinity values, show that the binding of the tested compounds is very strong.

EXAMPLE C: Four plate test

The products of the invention are administered by the oesophageal route to groups each comprising ten mice. One group is given syrup of gum. Thirty minutes after administration of the compounds to be studied the animals are placed in cages in which the floor is composed of four metallic plates. Each time the animal passes from one plate to another it receives a light electric shock (0.35 mA). The number of passages from one plate to another is recorded for one minute. After administration, the compounds of the invention significantly increase the number of passages from one plate to another, demonstrating the anxiolytic activity of the compounds of the invention.

EXAMPLE D: Action of the compounds of the invention on the circadian rhythm of locomotive activity of the rat The involvement of melatonin in reentrainment, by day/night alternation, the majority of physiological, biochemical and behavioural circadian rhythms has made it possible to establish a pharmacological model for research into melatoninergic ligands.

The effects of the molecules are tested on numerous parameters and, in particular, on the circadian rhythms of locomotive activity, which represent a reliable marker of the activity of the endogenous circadian clock.

In this study, the effects of such molecules on a particular experimental model, namely the rat placed in temporal isolation (permanent darkness), is evaluated.

Experimental protocol

One-month-old Long Evans male rats are subjected as soon as they arrive at the laboratory to a light cycle of 12 hours light per 24 hours (LD 12:12).

After 2 to 3 weeks' adaptation, they are placed in cages fitted with a wheel connected to a recording system in order to detect the locomotive activity phases and thus monitor the nychthemeral (LD) or circadian (DD) rhythms.

As soon as the recorded rhythms show a stable pattern in the LD light cycle 12:12 the rats are placed in permanent darkness (DD).

Two to three weeks later, when the free running (rhythm reflecting that of the endogenous clock) is clearly established, the rats are given a daily administration of the molecule to be tested.

The observations are made by means of visualisation of the rhythms of activity:

reentrainment of the rhythms of activity by the light rhythm, disappearance of the influence on the rhythms in permanent darkness, influence by the daily administration of the molecule; transitory or durable effect.

a software package makes it possible to measure the duration and intensity of the activity, the period of the rhythm of the animals during free running and during treatment, possibly to demonstrate by spectral analysis the existence of circadian and non-circadian (for example ultradian) components.

Results:

The compounds of the invention clearly appear to allow powerful action on the circadian rhythm via the melatoninergic system.

EXAMPLE E: Anti-arrhythinic activity

Protocol (Ref: LAWSON J. W. et al. J. Pharmacol. Expert. Therap., 1968, 160, pp. 22–31)

The test substance is administered intraperitoneally to a group of 3 mice 30 minutes before being subjected to anaesthesia with chloroform. The animals are then observed for 15 minutes. The absence of recording of arrhythmia and of cardiac frequencies higher than 200 beats/min (control: 400–480 beats/min) in at least two animals indicates significant protection.

EXAMPLE F: Pharmaceutical composition: tablets

| | |
|---|---|
| 1000 tablets each comprising 5 mg of N-Methyl-[4-(2,3-dihydro-1,4-benzoxathiin-5-yl)]-butanamide (Example 35) | 5 g |
| wheat starch | 20 g |
| maize starch | 20 g |
| lactose | 30 g |
| magnesium stearate | 2 g |
| silica | 1 g |
| hydroxypropylcellulose | 2 g |

We claim:

1. A compound selected from those of formula (I):

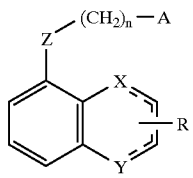

(I)

wherein:

X and Y, which may be identical or different, each represents sulphur, oxygen, $CH_q$ (where q is 0, 1, or 2), SO, or $SO_2$, with the proviso that X and Y cannot simultaneously represent $CH_q$ (where q is 0, 1 or 2), Z represents oxygen or $CH_2$, n is 0, 1, 2, 3 or 4, A represents

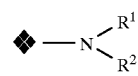

wherein $R^1$ represents hydrogen or linear or branched ($C_1$–$C_6$)-alkyl, and R² represents

wherein T represents
sulphur or oxygen and R³ represents
hydrogen, optionally substituted linear or branched ($C_1$–$C_6$)-alkyl, optionally substituted linear or branched ($C_2$–$C_6$)-alkenyl, optionally substituted linear or branched ($C_2$–$C_6$)-alkynyl, ($C_3$–$C_8$)-cycloalkyl, substituted ($C_3$–$C_8$)-cycloalkyl, cycloalkylalkyl, substituted cycloalkylalkyl, aryl, or arylalkyl,
or R³ represents

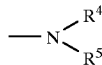

wherein R⁴ represents hydrogen
or linear or branched ($C_1$–$C_6$)-alkyl and R⁵ represents hydrogen, optionally substituted linear or branched ($C_1$–$C_6$)-alkyl, optionally substituted linear or branched ($C_2$–$C_6$)-alkenyl, optionally substituted linear or branched ($C_2$–$C_6$)-alkynyl, ($C_3$–$C_8$)-cycloalkyl, substituted ($C_3$–$C_8$)-cycloalkyl, cycloalkylalkyl, substituted cycloalkylalkyl, aryl, or arylalkyl,
or A represents

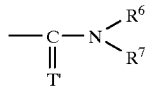

wherein
T' represents sulphur or oxygen,
R⁶ represents hydrogen or linear or branched ($C_1$–$C_6$)-alkyl
and R⁷ represents hydrogen, optionally substituted linear or branched ($C_1$–$C_6$)-alkyl, optionally substituted linear or branched ($C_2$–$C_6$)-alkenyl, optionally substituted linear or branched ($C_2$–$C_6$)-alkynyl, ($C_3$–$C_8$)-cycloalkyl, substituted ($C_3$–$C_8$)-cycloalkyl, cycloalkylalkyl, substituted cycloalkylalkyl, aryl, or arylalkyl,
R represents hydrogen, optionally substituted linear or branched ($C_1$–$C_6$)-alkyl, aryl, or arylalkyl,
the representation

denotes that those bonds may be single or double,
it being understood that two adjacent bonds cannot simultaneously be double and that the valency of the atoms is respected,
and wherein:
the term "aryl" denotes phenyl or naphthyl optionally substituted by one or more halogen, one or more OH, linear or branched ($C_1$–$C_6$)-alkyl, linear or branched ($C_1$–$C_6$)-alkoxy, cyano, nitro, amino, or trihaloalkyl, the term "arylalkyl" denotes linear or branched ($C_1$–$C_6$)-alkyl substituted by aryl as defined above,
the term "cycloalkylalkyl" denotes linear or branched ($C_1$–$C_6$)-alkyl substituted by one or more ($C_3$–$C_8$)-cycloalkyl,
the term "substituted" as applied to the terms "alkyl", "alkenyl" and "alkynyl" denotes that that group is substituted by one or more halogen, one or more OH and/or alkoxy,
the term "substituted" as applied to the terms "cycloalkyl" and "cycloalkylalkyl" denotes that the cyclic moiety is substituted by one or more halogen, one or more lineal or branched ($C_1$–$C_6$)-alkyl, linear or branched ($C_1$–$C_6$)-alkoxy, phenyl, hydroxy, or oxo,
with the proviso that
when Z is oxygen and one of X and Y is sulphur, the other cannot be $CH_2$,
$NR^1R^2$, Y cannot represent oxygen,
when Z represents oxygen, n is other than zero,
when Z represents oxygen and n is 1, A cannot represent $CONEt_2$,
when Z represents $CH_2$, n is 1 and A represents —$NR^1CSNR^4R^5$, R⁵ cannot represent aryl,
when X and Y simultaneously represent oxygen and the broken-line bonds are saturated, and R represents hydrogen or $CH_2OH$, then A is other than $NR^1R^{2a}$ wherein R¹ is as defined hereinbefore and $R^{2a}$ represents optionally substituted benzoyl, or its enantiomer or diastereoisomer, or its pharmaceutically-acceptable addition salt with an acid or base.

2. A compound of claim 1, wherein R represents hydrogen.

3. A compound of claim 1, wherein X and Y simultaneously represent oxygen.

4. A compound of claim 1, wherein X represents sulphur and Y represents oxygen.

5. A compound of claim 1, wherein X represents sulphur or oxygen and Y represents $CH_q$, (where q is 0, 1, or 2).

6. A compound of claim 1, wherein Z represents oxygen.

7. A compound of claim 1, wherein Z represents $CH_2$.

8. A compound of claim 1, wherein A represents $NR^1COR^3$.

9. A compound of claim 1, wherein A represents $CONR^6R^7$.

10. A compound of claim 1 which is N-methyl-[4-(2,3-dihydro-1,4-benzoxathiin-5-yl)]butanamide, or its enantiomer or diastereoisomer, or addition salt.

11. A compound of claim 1 which is N-ethyl-[4-(2,3-dihydro-1,4-benzoxathiin-5-yl)]butanamide, or its enantiomer or diastereoisomer, or addition salt thereof with a pharmaceutically acceptable acid or base.

12. A compound of claim 1 which is N-[3-(1,4-benzodioxin-5-propyl]-n-butanamide, or its enantiomer or diastereoisomer, or addition salt thereof with a pharmaceutically acceptable acid or base.

13. A compound of claim 1 which is N-methyl-[4-(2,3-dihydro-1,4-benzodioxin-5-yl)]butanamide, or its enantiomer or diastereoisomer, or addition salt thereof with a pharmaceutically acceptable acid or base.

14. A method for treating a living body afflicted with disorder of the melatoninergic system comprising the step of administering to the living body an amount of a compound of claim 1 which is effective for the alleviation of said condition.

15. A pharmaceutical composition useful for treating melatoninergic disorders comprising as active principle an effective amount of a compound as claimed in claim 1, together with one or more phaimaceutically-acceptable excipients or vehicles.

* * * * *

UNITED STATES PATENT AND TRADEMARK OFFICE
CERTIFICATE OF CORRECTION

PATENT NO. : 5,919,814
DATED : July 6, 1999
INVENTOR(S) : G. Guillaumet, I. Charton, A. Mamai, P. Renard, B. Pfeiffer, P. Delagrange
B. Guardiola It is certified that error appears in the above-identified patent and that said Letters Patent is hereby corrected as shown below:

Column 1,
Line 66: "melatoninieLgic" should read -- melatoninergic --.

Column 4,
Line 16: "succiniic," should read -- succinic --.

Column 5,
Line 63: "fonnula (I)," should read -- formula (I), --.
Line 66: "fomnula (Ib):" should read -- formula (Ib) :--.

Column 7,
Line 5: "foimula (I/e):" should read -- formula (I/e) : --.
Line 19: At the beginning of the line "einibefore" should read -- enibefore --.

Column 8,
Line 19: Insert -- : -- at the end of the line after "(I/h).
Line 32: "accordina" should read -- according --.
Line 34: ""noud" at the beginning of the line should read -- ound --.
Line 46 (approx): "particular case" at the beginning of the line should read
-- a particular case --.
Line 48: "liniear" should read -- linear --

Column 9,
Line 11: "ni" should read -- n, --.
Line 15: "coimpound" should read -- compound --.
Line 43: "paiticular" should read -- particular --.
Line 59: "paiticular" should read -- particular --.
Line 67: "putfted accordinlt" should read -- purified according --.

Column 10,
Line 67: "hereinbefebore" should read -- hereinbefore --.

Column 11,
Line 39: "i ncompound of for mula" should read -- compound of formula --.
Line 52: "folmula (II)." should read -- formula (II). --.

UNITED STATES PATENT AND TRADEMARK OFFICE
CERTIFICATE OF CORRECTION

PATENT NO. : 5,919,814
DATED : July 6, 1999
INVENTOR(S) : G. Guillaumet, I. Charton, A. Mamai, P. Renard, B. Pfeiffer, P. Delagrange
B. Guardiola It is certified that error appears in the above-identified patent and that said Letters Patent is hereby corrected as shown below:

Column 12,
Line 40 (approx): "folmula (II)," at the end of the line, should read -- formula (II), --.
Line 50: "-5-propyl]" should read -- -5-yl) -propyl] --.

Column 13,
Line 20: "accordin," should read -- according --.
Line 55: "roon" at the end of the line should read --room --.
Line 64: "benizodioxin" should read -- benzodioxin--.

Column 14,
Line 35: "puLe" should read -- pure --.
Line 37: "-Dihydm-" should read -- Dihydro --.

Column 15,
Line 14: "iodomethanie" at the beginning of the line, should read -- iodomethane --.
Line 15: "stirling" should read -- stirring --.
Line 40: "colouLless" should read -- colourless --.

Column 16,
Line 37: "pulre" should read -- pure --
Line 41: "coluimn" should read -- column --.
Line 51: "hydirogen" should read -- hydrogen --.

Column 17,
Line 28: "pule" at the beginning of the line should read -- pure --.

Column 19,
Line 14: "amnine" should read -- amine --.

Column 20,
Line 7: "agyents," should read -- agents, --.
Line 17: "dichloroinethaiie", should read -- dichloromethane --.
Line 18: "puiified" at the end of the line should read -- purified --.
Line 19: "tlash" should read "flash".
Line 39: "butenaniide" should read -- butenamide --.

UNITED STATES PATENT AND TRADEMARK OFFICE
CERTIFICATE OF CORRECTION

PATENT NO. : 5,919,814
DATED : July 6, 1999
INVENTOR(S) : G. Guillaumet, I. Charton, A. Mamai, P. Renard, B. Pfeiffer, P. Delagrange
B. Guardiola It is certified that error appears in the above-identified patent and that said Letters Patent is hereby corrected as shown below:

Column 21,
Line 53: "startin" at the end of the line should read -- starting --.

Column 22,
Line 19: "pyiidine" should read -- pyridine --.

Column 24,
Line 38: "pelmangan-" at the end of the line should read -- permangan- --.

Column 25,
Line 43, (approx.): "fomm" should read -- from --.

Column 26,
Line 8: "butanamnide" should read -- butanamide --.
Line 52: "magnesiumn" should read -- magnesium --.
Line 53: "silica el" should read -- silica gel --.

Column 27,
Line 51: "arson" should read -- argon --.
Line 63: "dichloromethanie" should read -- dichloromethane --.

Column 28,
Line 38: "diied" should read -- dried --.

Column 29,
Line 17: "ovemight" should read -- overnight --.
Line 24: "chlomatography" should read -- chromatography --.

Column 30,
Line 49: "canted" should read -- carried --.

Column 31,
Line 11, "pnimary" should read -- primary --.

Column 32,
Line 14 (approx.): "Anti-arrhythinic" should read -- Anti-arrhythmic --.
Line 55: Insert a comma -- , -- after the number "1".
Line 57: Insert a comma -- , -- after "3".

UNITED STATES PATENT AND TRADEMARK OFFICE
CERTIFICATE OF CORRECTION

PATENT NO.    : 5,919,814
DATED         : July 6, 1999
INVENTOR(S)   : G. Guillaumet, I. Charton, A. Mamai, P. Renard, B. Pfeiffer, P. Delagrange
                B. Guardiola It is certified that error appears in the above-identified patent and that said Letters Patent is hereby corrected as shown below:

Column 34,
Line 12: "lineal" at the end of the line should read -- linear --.
Line 44: After the word "salt" at the end of the line, insert -- thereof with a pharmaceutically-acceptable acid or base --.
Line 48: Insert a hyphen -- - -- between "pharmaceutically" and "acceptable".
Line 50: "-5-" should read -- -5-yl- --.
Line 52: Insert a hyphen -- - -- between "tically" and "acceptable".
Line 56: Insert a hyphen -- - -- between "pharmaceutically" and "acceptable".

Signed and Sealed this

Seventh Day of August, 2001

NICHOLAS P. GODICI
*Acting Director of the United States Patent and Trademark Office*